United States Patent [19]

Jacobsen

[11] Patent Number: Plant 6,423

[45] Date of Patent: Nov. 29, 1988

[54] ANNETTE HEGG DIVA STARLIGHT

[75] Inventor: Peter Jacobsen, Skibby, Denmark

[73] Assignee: Paul Ecke, Jr., Encinitas, Calif.

[21] Appl. No.: 6,424

[22] Filed: Jan. 23, 1987

[51] Int. Cl.[4] ..... A01H 5/00

[52] U.S. Cl. ..... Plt./86

[58] Field of Search ..... Plt./86

*Primary Examiner*—Robert E. Bagwill

*Attorney, Agent, or Firm*—Charles W. Rummler

[57] ABSTRACT

A new Poinsettia cultivar distinguished by a more intensive bract color than other red varieties of the Annette Hegg family and a homogenious growth, in that all individual plants are equal in size and vigor. The branches of this cultivar are noticeably strong; otherwise this new plant has retained the important self branching, easy rooting, low temperature blooming and medium height characteristics of the Annette Hegg family of poinsettias.

1 Drawing Sheet

BACKGROUND OF THE NEW PLANT

This new Poinsettia originated as a radiation induced mutation of the well known variety 'Annette Hegg Red' (U.S. Plant Pat. No. 2,962) and was produced by me at Skibby, Denmark. I selected this particular mutation because of its intensive red bract color and homogeneity, the bract color of this plant being brighter and quite different than that of any other of the Annette Hegg family. I propagated this new plant, by cuttings, through successive generations, which time and again has shown that not only has the intensive bract color held true from generation to generation, but that all plants vegetatively propagated from this new variety are extremely uniform in plant size and vigor.

DESCRIPTION OF THE DRAWINGS

My new variety of Poinsettia is illustrated by the accompanying full color photographic drawings, the upper one of which shows a full face view of the flower clusters and surrounding bracts and the lower view shows a typical potted plant in full bloom, the color rendition in both views being as true to that herein specified as is reasonably possible to obtain by conventional photographic procedures.

DESCRIPTION OF THE NEW PLANT

The following is a detailed description of this new Poinsettia variety as observed in greenhouse at Encinitas, Calif., in the fall of 1986, with color designations according to The R.H.S. Colour Chart published in 1966 by The Royal Horticultural Society at London, England.

THE PLANT

Origin: Mutation induced by irradiation.

Parentage: 'Annette Hegg Red' (U.S. Plant Pat. No. 2,962).

Classification:

*Botanic.*—*Euphorbia pulcherrima.*

*Commercial.*—Greenhouse Poinsettia.

Form: Shrub.

Height: About 48 cm.

Growth habit: As a single stem, upright and vigorous with many self branching side shoots. May require a growth regulator.

Branching: Upright with many stems producing a bushy, full appearance.

Growth rate: Very fast. Rooting occurs in 15 to 20 days under intermittent mist and the plant will bloom in about 8 weeks at a night temperature of 16 to 18 degrees C. during October and November. Under poor light conditions, a somewhat higher temperature may be required.

Foliage: Similar to other varieties of the Annette Hegg family with long leaf blades of medium width on petioles of medium length.

*Leaf shape.*—Typical leaves are broad obovate with weakly developed lobes.

*Color.*—Upper side — Between R.H.S. 139A and 147A. Under side — Near R.H.S. 137B-C.

*Retention.*—The foliage lasts very well, as with the Annette Hegg family varieties in general.

*Bracts.*—Generally there are 12 to 18 uniformly colored bracts whose overall size has a spread presentation diameter of about 36 cm. The bract petioles are somewhat twisted which results in the bract blades being in a twisted plane, thereby giving depth and a full appearance to the overall bract presentation. The length and width of the three primary bracts of the new variety are greater than those of Annette Hegg 'Dark Red' (U.S. Plant Pat. No. 3,160) and, in average, the individual primary bract blades are more than 13 cm. in length and about 11 cm. in width, with petioles that are about 6 cm. long.

*Shape.*—Obovate to elliptic with weakly developed lobes.

*Color.*—Upper side — Darker than 45B but brighter than 46A and near 46B. Under side — Between 45C and 45D. The bracts of this new cultivar are of a brighter color than other red varieties of the Annette Hegg family. The bract color does not have the blue-red shade of the 'Annette Hegg Dark Red' (U.S. Plant Pat. No. 3,160) or the 'Annette Hegg Lady' (U.S. Plant Pat. No. 3,764). Nor does the new plant have the orange-red of the 'Annette Hegg Diva' (U.S. Plant Pat. No. 3,763). The bract of the new plant has a brighter, almost fluorescent, red color than 'Annette Hegg Top Star' (U.S. Plant Pat. No. 4,164) or 'Annette Hegg Diamond' (U.S. Plant Pat. No. 4,641).

I claim:

1. A new and distinctive Poinsettia cultivar, substantially as herein shown and described, distinguished by the brighter red color than other red varieties of the Annette Hegg family.

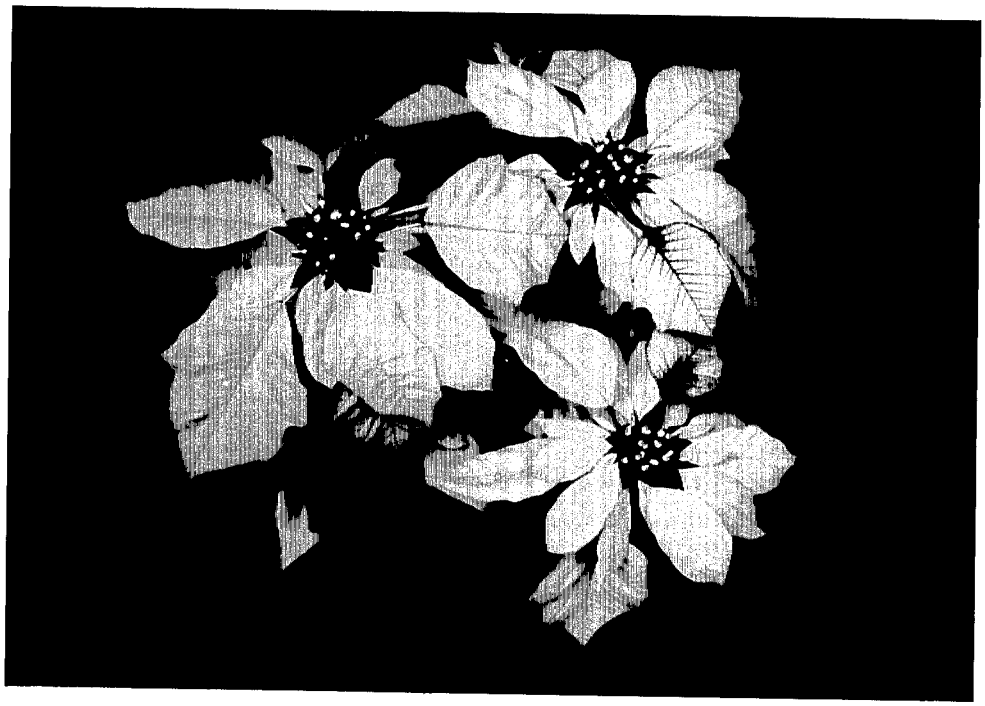
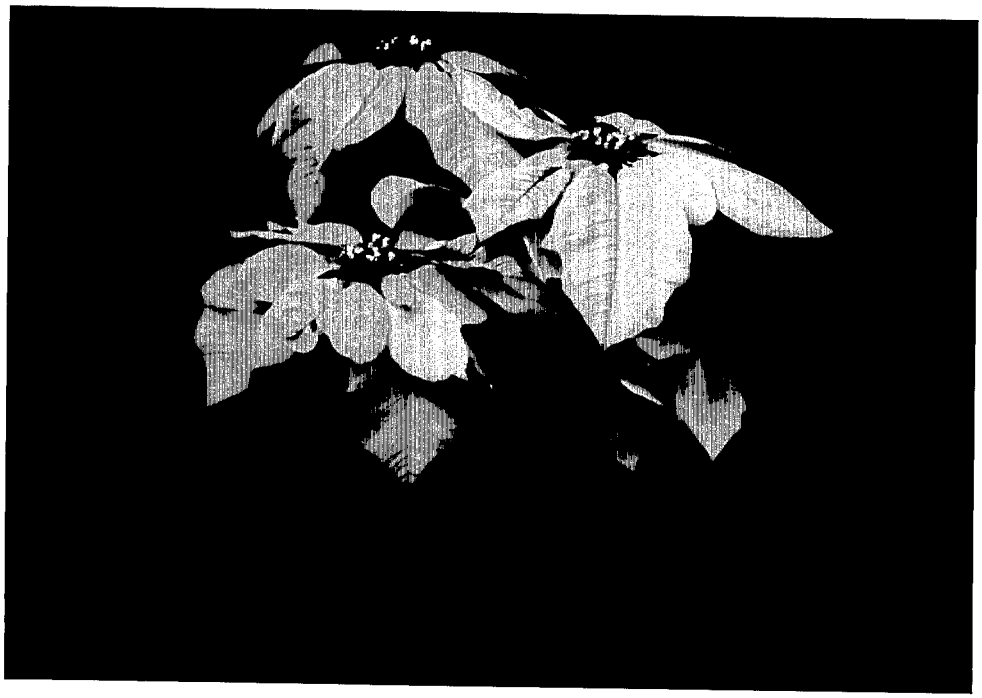

* * * * *